United States Patent [19]
Senzig et al.

[11] Patent Number: 6,023,494
[45] Date of Patent: *Feb. 8, 2000

[54] METHODS AND APPARATUS FOR MODIFYING SLICE THICKNESS DURING A HELICAL SCAN

[75] Inventors: Robert Senzig, Germantown; Jiang Hsieh, Waukesha, both of Wis.

[73] Assignee: General Electric Company, Schenectady, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/774,868

[22] Filed: Dec. 19, 1996

[51] Int. Cl.⁷ .................................................. G01N 23/00
[52] U.S. Cl. ................................................ 378/4; 378/15
[58] Field of Search .......................................... 378/4–20

[56] References Cited

U.S. PATENT DOCUMENTS 5,386,446 1/1995 Fujimoto et al. ....................... 378/20

Primary Examiner—Craig E. Church
Attorney, Agent, or Firm—Armstrong Teasdale LLP

[57] ABSTRACT

The present invention, in one form, is a method for modifying slice thickness during a helical scan without interrupting the scan. The method includes identifying adjacent and different regions within an object to be scanned. A transition region also is identified to include a portion of each of two adjacent regions and the interface therebetween. Slice thickness is modified during the scan so that redundant data is obtained in the transition region. Particularly, in one embodiment, a variable collimator is used to scan a first region with a first slice thickness. The variable collimator is rotated at the interface between the two adjacent regions, without interrupting table translation, to scan the second region with a second slice thickness. When changing the slice thickness, the collimator also is swept so that the x-ray beam with the second slice thickness re-scans a portion of the first region within the transition region. More particularly, the collimator is swept so that the transition region is scanned with both slice thicknesses.

20 Claims, 5 Drawing Sheets

METHODS AND APPARATUS FOR MODIFYING SLICE THICKNESS DURING A HELICAL SCAN

FIELD OF THE INVENTION

This invention relates generally to computed tomography (CT) imaging and more particularly, to modifying slice thickness during a CT system helical scan without interrupting the scan.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), Nov/Dec 1990.

In known CT systems, the x-ray beam from the x-ray source is projected through a pre-patient collimating device, or collimator, that defines the x-ray beam profile in the patient axis, or z-axis. The collimator typically includes x-ray absorbing material with an aperture therein for restricting the x-ray beam. Known apertures are typically linear, or rectangular, and the aperture width controls the slice thickness as measured along the z-axis. For example, by passing an x-ray beam through a collimator with a 10 mm aperture, i.e., a 10 mm collimator, the beam output from the collimator will have a 10 mm slice thickness.

Helical scans, as is known, typically are performed at a X:Y helical pitch, wherein helical pitch is the ratio of patient movement along the z-axis during one rotation of the x-ray source, X, to the slice thickness, Y, defined by the source collimator. For example, for a 1:1 helical pitch scan with a 5 mm collimator, the patient moves at a speed of approximately 5 mm/sec. Similarly, for a 1:1 helical pitch scan with a 10 mm collimator, the patient moves at a speed of approximately 10 mm/sec.

Slice thickness directly affects image resolution and scan efficiency. Particularly, smaller slice thicknesses typically provide a more detailed image resolution than larger slice thicknesses. However, larger slice thicknesses are more efficient than small slice thicknesses since more of the region is scanned with a large slice thickness in a shorter period of time.

Slice thickness, as is known, is related to both helical pitch and collimator size. Particularly, by reducing helical pitch, patient movement during x-ray source rotation is reduced, thus reducing the effective slice thickness, i.e., less of the patient is scanned during one gantry rotation. Slice thickness similarly is decreased by reducing collimator size. Alternatively, by increasing helical pitch, patient movement is increased thus increasing the effective slice thickness. Increasing the collimator size similarly increases the slice thickness.

Typically, an operator selects a slice thickness prior to a scan to optimize scan efficiency and image quality. Particularly, smaller slice thicknesses are preferable when scanning regions with multiple bony structures, i.e., when scanning the pancreas region. Larger slice thicknesses, however, are preferable when scanning regions with few bony structures, i.e., when scanning the liver region. Accordingly, and for example, an operator may choose a 10 mm collimator at a 1:1 helical pitch to scan a liver region, and the operator may choose a 5 mm collimator at a 1:1 helical pitch to scan a pancreas region.

Scans, however, often are performed for a region that includes different and adjacent sub-regions, i.e., a bony sub-region adjacent a non-bony sub-region. To optimize image quality and scan efficiency for such regions, an operator typically must use a "compromise" collimator size. Accordingly, the bony sub-regions are scanned with an overly broad slice thickness and the non-bony regions are scanned with an overly thin slice thickness. Scans with such "compromise" collimation, accordingly, are neither efficient nor practical for optimizing system performance and image quality.

Known methods of improving image quality and scan efficiency when scanning adjacent bony and non-bony regions typically include altering slice thicknesses during a scan. Particularly, different x-ray source collimators or different helical pitches are selected when scanning the different regions. For example, a 10 mm collimator may be used when scanning a region with few bony structures and a 3 mm collimator may be used when scanning a region with many bony structures. However, such methods require interrupting the scan before changing the helical pitch of the collimator. Until now, it was believed that failure to interrupt the scan when changing the slice thickness would cause a loss of data and a degradation in image quality. Accordingly, the known methods are both time consuming and inefficient.

It would be desirable to modify slice thickness during a scan without interrupting the scan. It also would be desirable to modify slice thickness without significantly increasing the processing time and without significantly decreasing image quality.

SUMMARY OF THE INVENTION

These and other objects may be attained by a method which, in one embodiment, facilitates modifying slice thickness in a computed tomography system without interrupting a scan and without degrading image quality. Particularly, before scanning a patient, adjacent anatomy regions having different amounts of bony structures are identified. A transition region also is identified to include a portion of two different regions and the interface between such different regions. During a helical scan, slice thickness is modified, without stopping table translation, to obtain redundant data corresponding to the transition region.

More specifically, in accordance with one embodiment of the present invention, a patient is scanned with a first collimator size and a first patient table speed, i.e., with a first slice thickness. When the table has translated so that the collimator is substantially aligned with the interface between different regions, the collimator size is modified, i.e., decreased or increased, to scan the patient with a second slice thickness. In addition, the collimator is swept, or rotated, so that the path of the x-ray beam collimated by the new collimator size overlaps a portion of the path of the x-ray beam collimated by the first collimator size. Specifically, the collimator is swept so that the path of the x-ray beam collimated by the new collimator size overlaps the path of the x-ray beam collimated with the first collimator size within the transition region. Accordingly, data is obtained for the entire patient without interrupting the scan or stopping table translation. The data, including the redundant data, is then processed to generate images of the patient anatomy.

In another embodiment, and rather than sweeping the collimator, table speed is modified at the transition region to modify slice thickness without interrupting a helical scan. Particularly, when the table has translated so that the collimator is substantially aligned with the interface between different regions, the collimator size is modified to scan the patient with a second slice thickness. In addition, the table speed is reduced at the transition region so that the path of the x-ray beam collimated by the new collimator size overlaps a portion of the path of the x-ray beam collimated by the first collimator size. Accordingly, data is obtained for the entire patient without interrupting the scan or stopping table translation, and redundant data is collected within the transition region. The data, including the redundant data, is then processed to generate images of the patient anatomy.

In yet another embodiment, and rather than changing collimator size, helical pitch is modified at the transition region to modify slice thickness without interrupting a helical scan. More specifically, without modifying the collimator, the table speed is reduced, but not stopped, at the transition region. Accordingly, data is obtained for the entire patient without interrupting the scan or stopping table translation. The data is then processed to generate images of the patient.

In still another embodiment, the collimator size is modified without either sweeping the collimator or modifying table speed. Particularly, a collimator including at least two opposing blades that may be opened and closed to change the aperture width is used for scanning a patient. The patient is scanned with a first collimator size, i.e., with opposing blades opened to a first width. When the table has translated so that the collimator is substantially aligned with the interface between different regions, the collimator size is modified, i.e., the opposing blades are opened or closed, to scan the patient with a second slice thickness. Opening or closing the opposing blades in the transition region does not result in significant data loss for such region. Accordingly, data is obtained for the entire patient without interrupting the scan or stopping table translation, and such data is processed to generate images of the patient anatomy.

The methods described above modify slice thickness during a helical scan without interrupting the scan. Such methods also do not significantly increase the processing time and does not significantly decrease image quality.

DETAILED DESCRIPTION OF THE DRAWINGS

Figure 1:
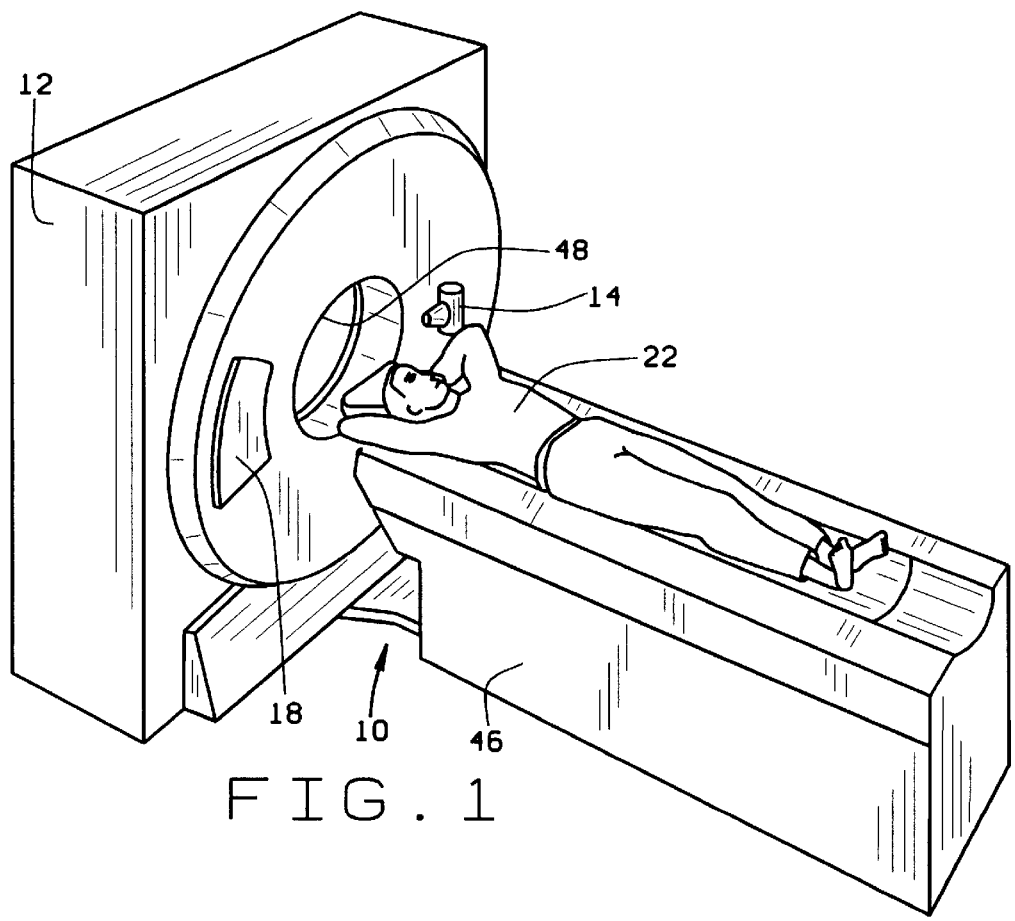
FIG. 1 is a pictorial view of a CT imaging system.
Figure 2:
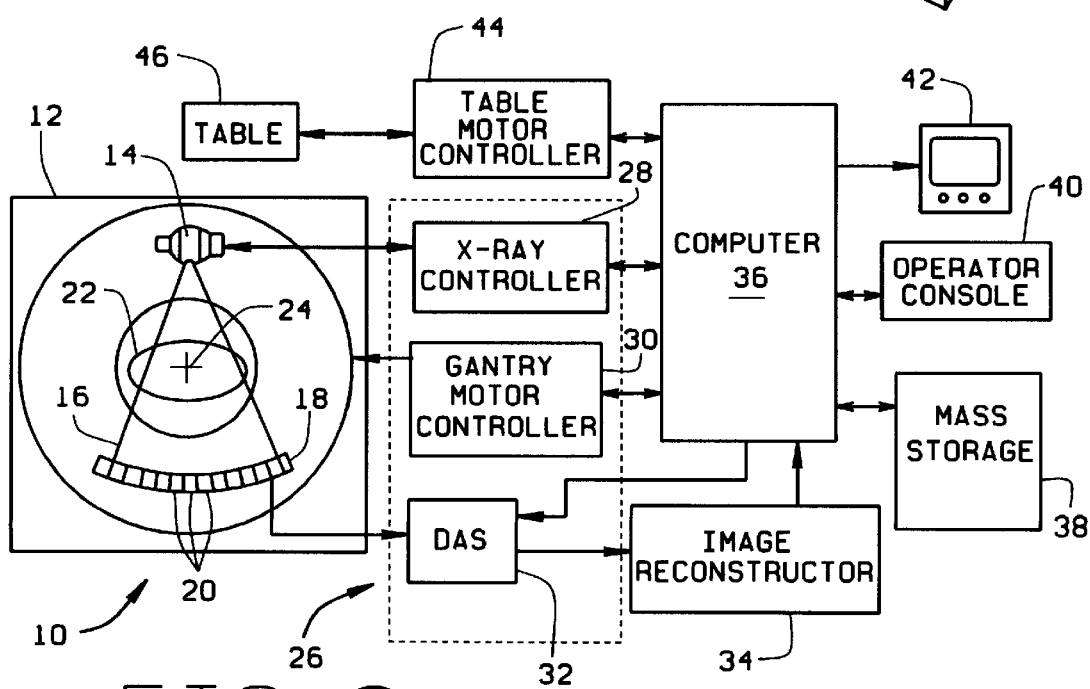
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
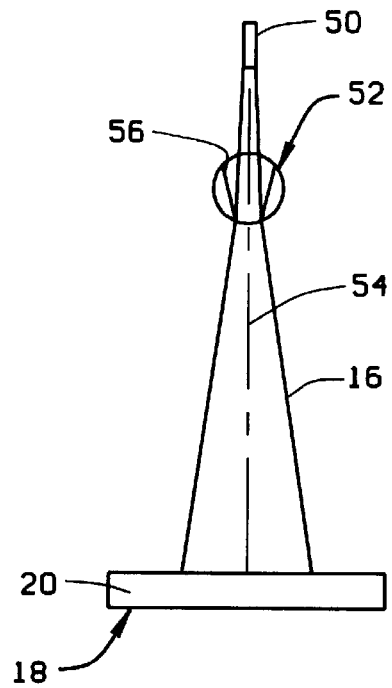
FIG. 3 is a schematic view of a CT imaging system with a variable collimator.

Referring to FIG. 3, and with respect to operation of x-ray source 14, x-ray beam 16 emanates from a focal spot 50 of source 14 (not shown in FIG. 3). X-ray beam 16 is collimated by a variable collimator 52, and collimated beam 16 is projected toward detector array 18 along a fan beam axis 54 centered within fan beam 16.

Collimator 52 has a substantially circular cross-sectional shape and an aperture 56 extends through variable collimator 52. A plurality of other collimator apertures (not shown) also are formed in and extend through variable collimator 52, and each aperture corresponds to a particular slice thickness, or slice width. For example, aperture 56 may correspond to a 10 mm slice width and another aperture may correspond to a 5 mm slice width. If a scan is to be performed for a 10 mm slice, then aperture 56 is aligned with expected x-ray focal spot 50 and restricts beam 16 projected from focal spot 50 to 10 mm. Similarly, if a scan is to be performed for a 5 mm slice, then an aperture 58 (not shown in FIG. 3) corresponding to a 5 mm slice width is aligned with expected x-ray focal spot 50 to restrict beam 16 to 5 mm. Variable collimator 52 is well known in the art.

The anatomy of patient 12 includes a plurality of different regions which preferably are scanned with different slice widths. For example, 5 mm slice widths typically are preferable when scanning the pancreas region, which includes multiple bony structure, and 10 mm slice widths typically are preferable when scanning the liver region, which includes few bony structures. Accordingly, and to scan both the liver region and the pancreas region, slice width preferably is changed in accordance with the region, i.e., pancreas or liver, being scanned.

Figure 4A:
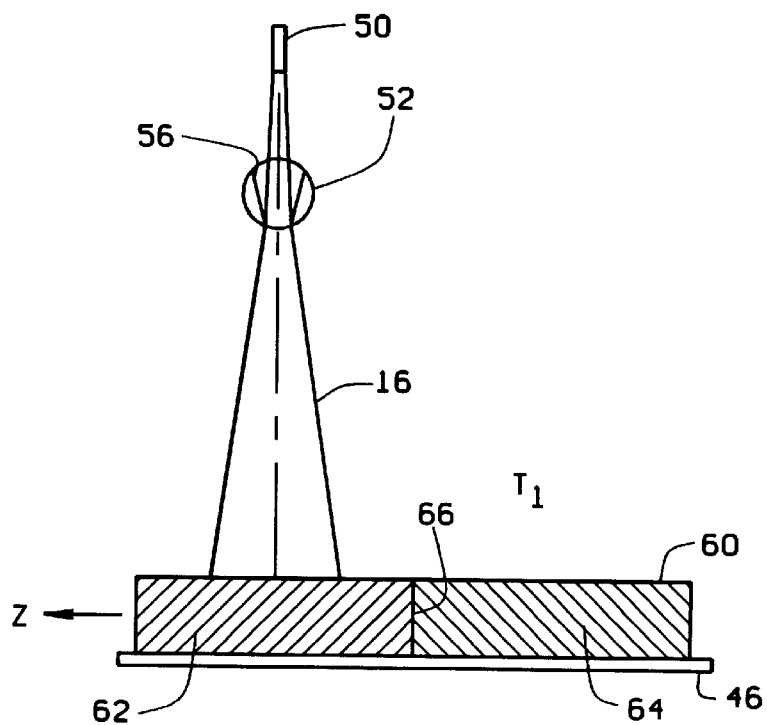
FIGS. 4a and 4b illustrate, at times $T_1$ and $T_2$, an x-ray focal spot, a variable collimator, and a region being scanned.
Figure 4B:
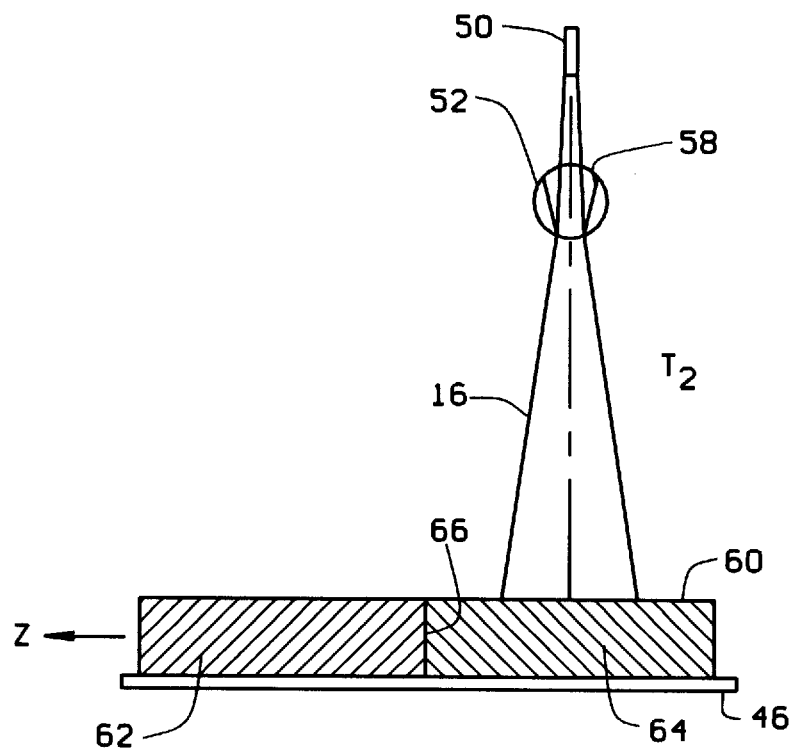

FIGS. 4a and 4b illustrate x-ray focal spot 50, variable collimator 52, and a region to be scanned 60 positioned on table 46 at times $T_1$ and $T_2$. Region being scanned 60 includes a liver region 62 and a pancreas region 64. Liver region 62, as explained above, includes few bony structures and pancreas region 64 includes many bony structures. In addition, liver region 62 is substantially adjacent pancreas region 64 at an interface 66. At time $T_1$, as shown in FIG. 4a, 10 mm collimator aperture 56 is aligned with x-ray focal spot 50 to restrict beam 16 to 10 mm while scanning liver region 62.

During a helical scan, table 46, and thus region to be scanned 60, translates along the z-axis in the direction indicated in the FIG. 4a. Accordingly, at time $T_2$, x-ray source focal spot 50 is aligned with pancreas region 64. Accordingly, collimator 52 is positioned, or rotated so that 5 mm collimator aperture 58 is aligned with focal spot 50 to restrict beam 16 to 5 mm while scanning pancreas region 64.

In accordance with known methods, collimator 52 is rotated to change slice widths approximately at the same time that x-ray focal spot 50 is aligned with interface 66. However, and until now, the scan must be interrupted when changing the collimator size to avoid losing any data.

Similarly, and until now, the scan must be interrupted when changing table speed, e.g., helical pitch, to modify scan widths.

In accordance with one embodiment of the present invention, slice widths are modified without interrupting a scan. In addition, slice widths are modified without significantly degrading image quality.

The following discussion of slice width modification sometimes refers specifically to helical scans of a region including a liver region and a pancreas region. Such slice width modification is not, however, limited to such scan regions, and may be used with other regions of the patient anatomy, e.g., the shoulder and head regions.

Figure 5:
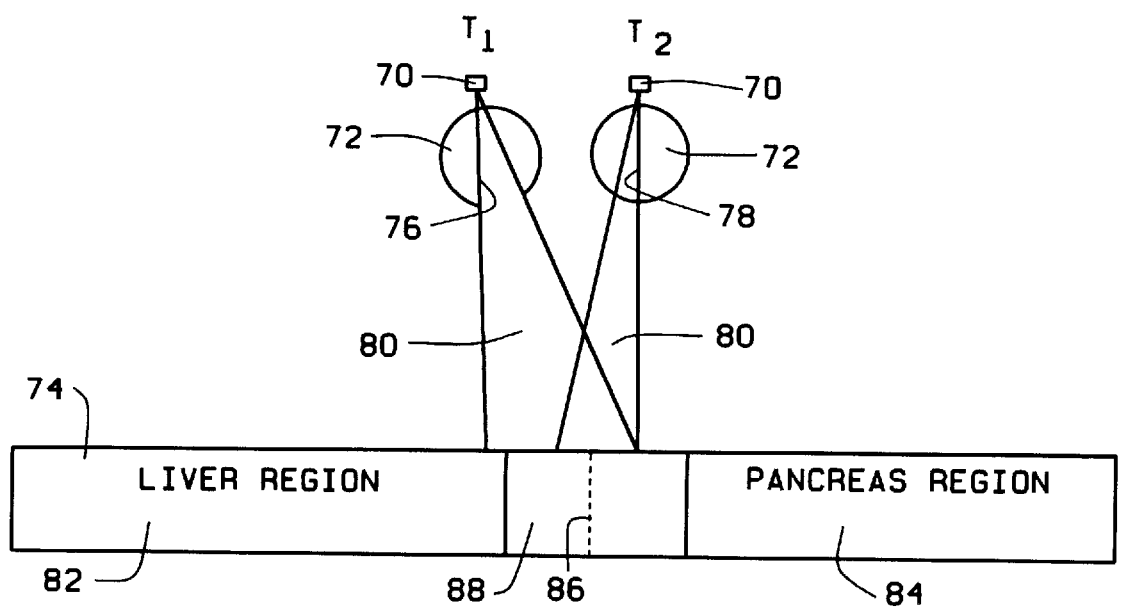
FIG. 5 illustrates an x-ray focal spot, a variable collimator, and a region to be scanned at times $T_1$ and $T_2$ in accordance with one embodiment of the present invention.

FIG. 5 illustrates an x-ray focal spot 70, a variable collimator 72, and a region to be scanned 74 positioned on table 46 at times $T_1$ and $T_2$ in accordance with one embodiment of the present invention. Variable collimator 72 has a substantially circular cross-sectional shape and includes at least two apertures 76 and 78 extending therethrough. Each aperture 76 and 78 corresponds to a different slice thickness. Particularly, aperture 76 is approximately 10 mm to correspond with a 10 mm slice thickness, and aperture 78 is approximately 5 mm to correspond to a 5 mm slice thickness. X-ray beam 80 is collimated by variable collimator 72, and collimated beam 80 is projected toward region to be scanned 74 along a fan beam axis centered within fan beam 80.

Region to be scanned 74 includes a liver region 82 and a pancreas region 84. Liver region 82, as explained above, includes few bony structures and pancreas region 84 includes many bony structures. In addition, liver region 82 is substantially adjacent pancreas region 84 at an interface 86. At time $T_1$, 10 mm collimator aperture 76 is aligned with x-ray focal spot 70 to restrict x-ray beam 80 to 10 mm, however at time $T_2$, 5 mm collimator aperture 78 is aligned with x-ray focal spot 70 to restrict x-ray beam 80 to 5 mm.

In accordance with one embodiment of the present invention, a transition region 88 is identified to correspond to interface 86 between liver region 82 and pancreas region 84. As shown in FIG. 5, transition region 88 includes a portion of liver region 82, interface 86, and a portion of pancreas region 84. Transition region 88 may be determined, for example, by performing a scout view to identify the location of transition region 88. Scout views are well known. Alternatively, the location of transition region 88 may be manually determined explicitly with known anatomical landmarks. The location of transition region 88 may be stored, for example, in mass storage 38 of computer 36. Slice thickness then is modified utilizing transition region 88 without interrupting the scan.

In operation, table 46 and region to be scanned 74 are continuously translated through gantry opening 48 (FIG. 1) to helically scan region 74. As described above, it typically is preferable to scan liver region 82 and pancreas region 84 with different slice thickness. At a time before time $T_1$, focal spot 70 is substantially aligned with liver region 82, and collimator 72 is oriented so that 10 mm collimator aperture 76 is aligned with x-ray focal spot 70 to restrict x-ray beam 80 to 10 mm along liver region 82, i.e., collimator 72 is oriented to scan liver region 82 with a first slice thickness.

Without interrupting the scan, i.e., without stopping table translation, collimator 72 then is changed, or rotated, when focal spot 70 is substantially aligned with interface 86. Particularly, collimator 72 is rotated so that 5 mm collimator aperture 78 is aligned with x-ray focal spot 70 to restrict x-ray beam 80 to 5 mm, i.e., the first slice thickness is modified to a second slice thickness. To avoid data loss which might otherwise occur while simultaneously changing collimator 72 and translating table 46, collimator 72 is swept both before and after changing collimator aperture 76 from 10 mm to 5 mm. Particularly, at time $T_1$ before focal spot 70 and collimator aperture 76 are aligned with transition region 88, collimator 72 is gradually swept forward so that collimator aperture 76 directs 10 mm x-ray beam along the z-direction to impinge at least a portion of transition region 88. At time $T_2$ after collimator 72 has been changed, collimator 72 is swept backwards so that collimator aperture 78 directs 5 mm x-ray beam 80 along the z-direction to overlap at least a portion of the x-ray beam projected at time $T_1$ in transition region 88. Accordingly, duplicative, i.e., redundant, data is obtained for region to be scanned 74 along transition region 88. Specifically, data corresponding to both the 10 mm slice thickness and the 5 mm slice thickness is obtained for transition region 88. After collimator 72 has been swept backwards, collimator 72 is gradually swept forward to direct x-ray beam 80 in a substantially vertical direction so that the x-ray beam axis is substantially perpendicular to pancreas region 84. For example, collimator 72 may be swept forward after table 46 translates a sufficient distance for backward swept x-ray beam 80 to impinge only pancreas region 84.

The data acquired during the single scan is then processed, in accordance with known methods, to generate images of a plurality of views of region to be scanned 74. Either the 5 mm slice thickness data or the 10 mm slice thickness data may be processed in connection with images corresponding to transition region 88. In one embodiment, data corresponding to the 5 mm slice thickness is used for image reconstruction for views within transition region 88. However, data corresponding to the 10 mm slice thickness may be used. Alternatively, redundant data corresponding to both of the different slice thicknesses may be used, e.g., interpolated, for image reconstruction within transition region 88. Therefore, and with respect to transition region 88, either 10 mm slice thickness data, 5 mm slice thickness data, or interpolated data may be used for image reconstruction.

For the above-described method, the location of the transition region is predetermined and stored in mass storage 38 of computer 36. Similarly, predetermined slice thicknesses, or collimator sizes, also are stored in mass storage 38 of computer 36. Alternatively, an operator may change collimator sizes via console 40 during the scan.

Using the above-described method, slice thickness is modified and data is acquired for entire region to be scanned 74 without interrupting the scan. Specifically, entire liver region 82 is scanned with a 10 mm slice thickness and entire pancreas region 84 is scanned with a 5 mm thickness without interrupting table translation and by sweeping collimator 72 both before and after changing collimator 72. However, slice thickness also may be modified by sweeping collimator 72 only before changing collimator 72. Similarly, slice thickness may be modified by sweeping collimator 72 only after changing collimator 72.

Figure 6:
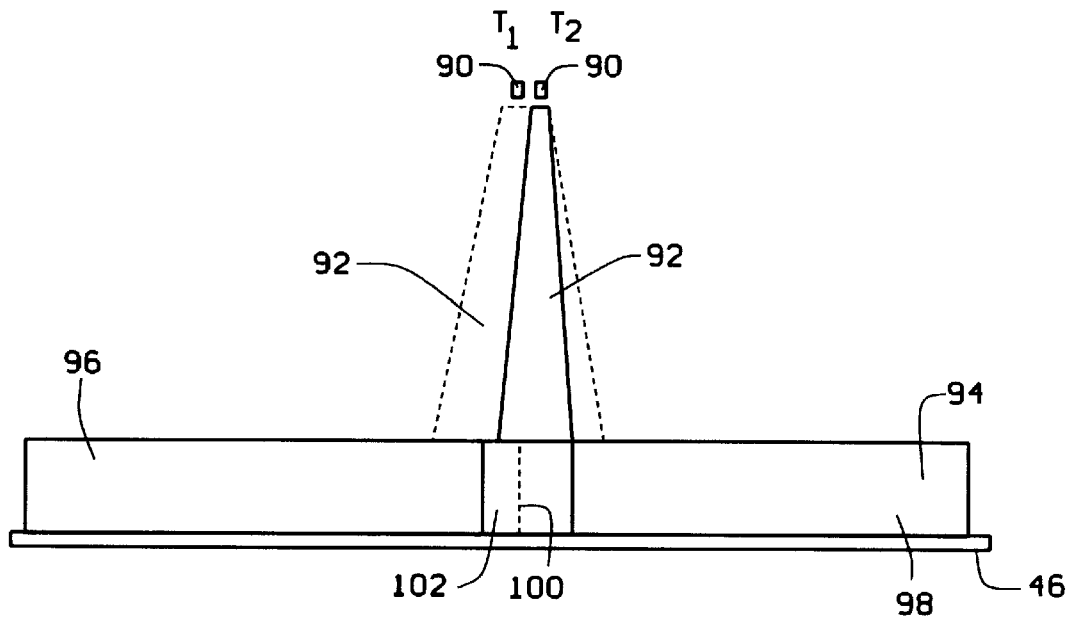
FIG. 6 illustrates an x-ray focal spot projecting an x-ray beam towards a region to be scanned at times $T_1$ and $T_2$ in accordance with another embodiment of the present invention.

In accordance with another embodiment of the present invention, and rather than sweeping collimator 72, data loss which might otherwise occur while simultaneously changing collimator 72 and translating table 46 is avoided by modifying table speed in the transition region. Particularly, FIG. 6 illustrates an x-ray focal spot 90 projecting an x-ray beam 92 towards a region to be scanned 94 positioned on table 46 at times $T_1$ and $T_2$. At time $T_1$, a collimator (not shown in FIG. 6) such as collimator 72 is oriented so that a 10 mm collimator aperture is aligned with x-ray focal spot 90 to restrict x-ray beam 92 to 10 mm. At time $T_2$, however, the collimator is oriented so that a 5 mm collimator aperture is aligned with x-ray focal spot 90 to restrict x-ray beam 92 to 5 mm.

Region to be scanned 94 includes a liver region 96 and a pancreas region 98. Liver region 96, as explained above, includes substantially less detailed structures, e.g., few bony structures, and pancreas region 98 includes substantially more detailed structures, e.g., many bony structures. In addition, liver region 96 is substantially adjacent pancreas region 98 at an interface 100. A transition region 102 is identified to correspond to interface 100 between liver region 96 and pancreas region 98, and includes a portion of liver region 96, interface 100, and a portion of pancreas region 98. Transition region 102 may be determined and stored as described above.

In operation, table 46 and region to be scanned 94 are continuously translated through gantry opening 48 (FIG. 1) to helically scan region 94. As described above, it typically is preferable to scan liver region 96 and pancreas region 98 with different slice thickness. At time $T_1$, focal spot 90 is substantially aligned with liver region 96, and the collimator is oriented so that a 10 mm aperture is aligned with x-ray focal spot 90 to restrict x-ray beam 92 to 10 mm along liver region 96. Accordingly, when focal spot 90 and the collimator aperture are substantially aligned with interface 100, x-ray beam 92 impinges approximately 5 mm of pancreas region 98 and 5 mm of liver region 96.

Without interrupting the scan, i.e., without stopping table translation, the collimator is changed, or rotated, when focal spot 90 is substantially aligned with interface 100. Particularly, collimator 72 is rotated so that a 5 mm collimator aperture is aligned with x-ray focal spot 90 to restrict x-ray beam 90 to 5 mm, i.e., the first slice thickness is modified to a second slice thickness. To avoid data loss which might otherwise occur while simultaneously changing the collimator and translating table 46, the speed of table translation is reduced without stopping table 46. Particularly, while changing the collimator, the speed of table translation is reduced so that at time $T_2$ after the collimator has been changed, the collimator aperture directs 5 mm x-ray beam 92 along the z-direction to overlap at least a portion of the x-ray beam projected at time $T_1$ in transition region 102. Accordingly, duplicative, i.e., redundant, data is obtained for region to be scanned 94 along transition region 102. Specifically, data corresponding to both the 10 mm slice thickness and the 5 mm slice thickness is obtained for transition region 102. The data acquired during the scan may then be used, as described above, to generate images of a plurality of views of region to be scanned 74.

As one specific example, assume that helical pitch is set to 1:1 when scanning liver region 96. Accordingly, to scan liver region 96 with a 10 mm slice thickness, table 46 translates at an approximate speed of 10 mm per second. Similarly, if pancreas region 98 is scanned with the same helical pitch, then table translation speed is reduced from 10 mm per second to 5 mm per second during transition region 102. To ensure that a portion of 5 mm x-ray beam 92 overlaps a portion of 10 mm x-ray beam 92, table speed may be reduced at interface 102 to approximately, for example, 2 mm per second.

Figure 7:
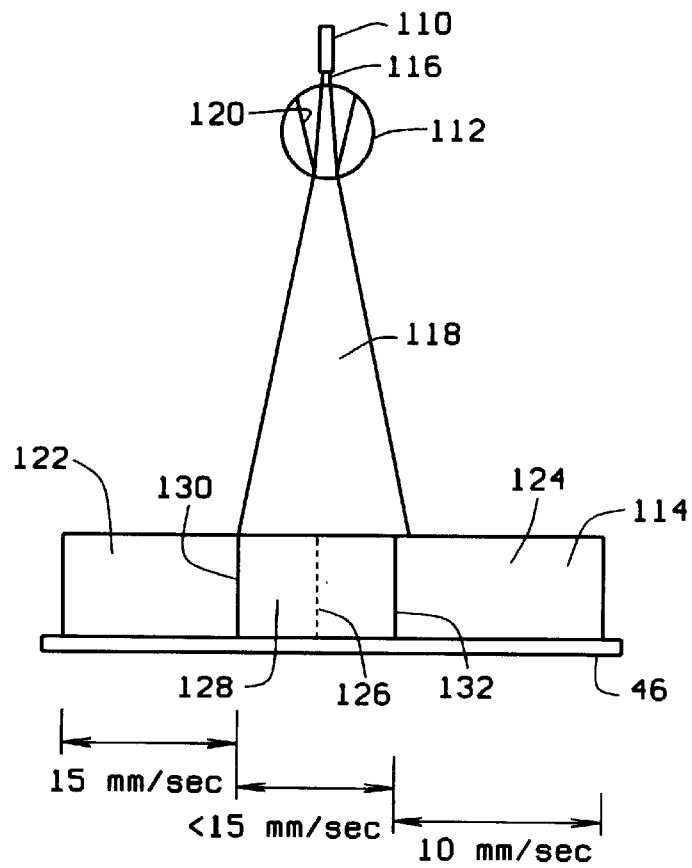
FIG. 7 illustrates an x-ray focal spot, a collimator, and a region to be scanned in accordance with yet another embodiment of the present invention.

In accordance with another embodiment of the present invention, and rather than modifying the collimator, slice thickness is modified without interrupting a scan by modifying helical pitch. Particularly, FIG. 7 illustrates an x-ray focal spot 110, a collimator 112, and a region to be scanned 114 positioned on table 46. Uncollimated x-ray beam 116 is collimated by collimator 112, and collimated beam 118 is projected toward region to be scanned 114. Collimator 112 has a substantially circular cross-sectional shape and an aperture 120 extends through collimator 112. A plurality of other collimator apertures (not shown) also may be formed in and extend through variable collimator 112, and each aperture corresponds to a particular slice thickness, or slice width.

Region to be scanned 114 includes a liver region 122 and a pancreas region 124. Liver region 122, as explained above, includes substantially less detailed structures, e.g., few bony structures, and pancreas region 124 includes substantially more detailed structures, e.g., many bony structures. In addition, liver region 122 is substantially adjacent pancreas region 124 at an interface 126. A transition region 128 is identified to correspond to interface 126 between liver region 122 and pancreas region 124, and includes a portion of liver region 122, interface 126, and a portion of pancreas region 124. Transition region 128 may be determined and stored as described above.

Assume that helical pitch is set to 1.5:1 when scanning liver region 122, wherein helical pitch is the ratio of table 46 movement in one rotation of the x-ray source 14 to the slice width, or slice thickness, defined by collimator 112. Accordingly, to scan liver region 122 with a 10 mm collimator aperture, table 46 translates at an approximate speed of 15 mm per second. To scan pancreas region 124 with a smaller slice thickness, helical pitch may be changed, for example, to 1:1 when scanning pancreas region 124. To scan pancreas region 124 with a 10 mm collimator aperture, table 46 translates at an approximate speed of 10 mm per second. Accordingly, modifying helical pitch facilitates modifying slice thickness without changing collimator 112.

In operation, table speed is modified utilizing transition region 128. Particularly, when collimator 112 and focal spot 110 are substantially aligned with start 130 of transition region 128, table translation speed is reduced to be slower than 15 mm per second, i.e., the table speed used for scanning liver region 122. While collimator 112 and focal spot 110 are substantially aligned with transition region 128, table translation speed is reduced so that when collimator 112 and focal spot 110 are substantially aligned with an end 132 of transition region 128, table translation speed is approximately 10 mm per second. Reducing table translation speed from 15 mm per second to 10 mm per second during transition region 128 substantially prevents data loss which may otherwise occur when changing slice thickness at interface 126.

The above-described embodiment facilitates modifying slice thickness during a scan without interrupting the scan. In addition, the described embodiment facilitates obtaining adequate data for transition regions between the liver and the pancreas without changing collimators or collimator sizes. It is to be understood, however, that other embodiments may be utilized to modify slice thickness during a scan in accordance with the principles set forth above.

Figure 8:
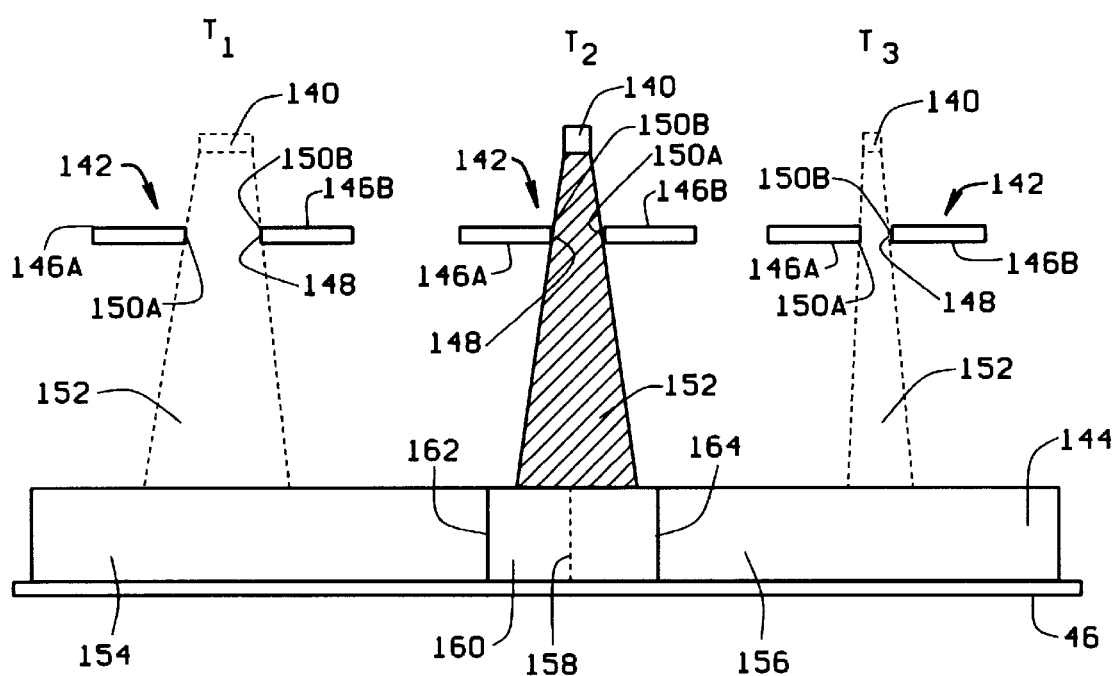
FIG. 8 illustrates an x-ray focal spot, a collimator, and a region to be scanned at times $T_1$, $T_2$, and $T_3$ in accordance with still another embodiment of the present invention.

For example, FIG. 8 illustrates an x-ray focal spot 140, a collimator 142, and a region to be scanned 144 positioned on table 46 at times $T_1$, $T_2$, and $T_3$ in accordance with still another embodiment of the present invention. Collimator 142 includes two opposing and adjustably spaced metallic elements 146A and 146B, such as blades. An aperture 148 is formed between blades 146A and 146B, and is defined by edges 150A and 150B of blades 146A and 146B, respectively. An x-ray beam 152 is collimated by collimator 142, and collimated beam 152 is projected toward region to be scanned 144 along a fan beam axis centered within fan beam 152.

Region to be scanned 144 includes a liver region 154 and a pancreas region 156. Liver region 154, as explained above, includes substantially less detailed structures and pancreas region 156 includes substantially more detailed structures. In addition, liver region 154 is substantially adjacent pancreas region 156 at an interface 158. At time $T_1$, opposing collimator blades 146A and 146B are spaced a first distance apart, e.g., a first width, so that aperture 148 is approximately 10 mm, and so that collimator aperture 148 is aligned with x-ray focal spot 140 to restrict x-ray beam 152 to 10 mm. At time $T_2$, opposing collimator blades 146A and 146B are spaced a second distance apart, e.g., a second width, so that aperture 148 is less than 10 mm, and so that collimator aperture 148 is aligned with x-ray focal spot 140 to restrict x-ray beam 152 to 5 mm. However, at time $T_3$, opposing collimator blades 146A and 146B are spaced at a third distance apart, e.g., a third width, so that aperture 148 is approximately 5 mm, and so that collimator aperture 148 is aligned with x-ray focal spot 140 to restrict x-ray beam 152 to 5 mm.

A transition region 160 is identified to correspond to interface 158 between liver region 154 and pancreas region 156. As shown in FIG. 8, transition region 160 includes a portion of liver region 154, interface 158, and a portion of pancreas region 156. Transition region 160 may be determined and stored, for example, as described above.

In operation, table 46 and region to be scanned 144 are continuously translated through gantry opening 48 (FIG. 1) to helically scan region 144. As described above, it typically is preferable to scan liver region 154 and pancreas region 156 with different slice thickness. As previously described, at time $T_1$, focal spot 140 is substantially aligned with liver region 154, and collimator 142 is oriented so that 10 mm collimator aperture 148 is aligned with x-ray focal spot 140 to restrict x-ray beam 152 to 10 mm along liver region 154.

Without interrupting the scan, i.e., without stopping table translation, collimator 142 then is changed when focal spot 140 is substantially aligned with a start 162 of transition region 160. Particularly, at least one of collimator blades 146A and 146B is moved relative to the other collimator blade so that collimator aperture 148 is reduced from 10 mm to 5 mm. For example, when focal spot 140 is substantially aligned with start 162 of transition region 160, each blade 146A and 146B is moved toward the other blade 146A and 146B, respectively, so that at time $T_2$, collimator aperture 148 is, for example, 7 mm. Alternatively, only one blade 146A and 146B may be moved to modify the size of collimator aperture 148. When focal spot 140 is substantially aligned with and end 164 of transition region 160, collimator blades 146A and 146B are positioned so that collimator aperture 148 is approximately 5 mm. Accordingly, data is obtained for entire region to be scanned 144 without either modifying table translation speed or changing a rotatable collimator. The data is then processed in accordance with known methods to generate images of a plurality of views of region to be scanned 144.

While the above-described scan thickness modification embodiments refer to determining the transition region prior to executing the helical scan, such modifications may be performed dynamically during the scan. Particularly, helical artifacts are known to be caused by inconsistency between the start and end of a scan. This inconsistency can be measured in accordance with known techniques. The measured inconsistency may then be used to modify scan thickness. For example, if the measured inconsistency is large, then slice thickness may be decreased without interrupting the scan, as described above, to improve image quality. Alternatively, if the measured inconsistency is small, then the slice thickness may be increased without interrupting the scan, as described above, to increase scan efficiency.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, the above-described embodiments also may be used in connection with multislice CT systems. In addition, while scans performed above were described in connection with the pancreas and liver regions, the scans may be performed with other regions, including the entire patient. Furthermore, while collimator 142 included two opposing blades, other collimators, such as collimators including two cylinders, may be used in connection with the above-described embodiments. Accordingly, the spirit and scope of the invention are to be limited only by the terms of the appended claims.

What is claimed is:

1. A method for modifying slice thickness of a tomography system during a helical scan of an object of interest with an x-ray beam, the object of interest comprising a first region and a second region having a different structure than the first region, said method comprising the steps of:

scanning the first region of the object of interest with a first slice thickness;

identifying a transition region intermediate the first region and the second region of the object of interest;

collecting redundant data for the transition portion with first and second slice thicknesses without interrupting the scan; and scanning the second region of the object of interest with the second slice thickness without interrupting the scan.

2. A method in accordance with claim 1 wherein the imaging system includes a gantry having an opening therein and a patient table, and wherein scanning the object of interest with a first slice thickness comprises the step of translating the table through the gantry opening at a first table speed.

3. A method in accordance with claim 2 wherein collecting redundant data for the transition portion without interrupting the scan comprises the step of scanning at least a portion the transition region with the first slice thickness and a second slice thickness without stopping the table translation.

4. A method in accordance with claim 3 wherein the imaging system includes an x-ray source for emitting an x-ray beam and a collimator having a first aperture therein for collimating the x-ray beam, and wherein scanning the object of interest with a first slice thickness comprises the step of aligning the collimator first aperture with the x-ray source.

5. A method in accordance with claim 4 wherein the collimator includes a second aperture therein, the second aperture having a different size than the first aperture, and wherein scanning at least a portion the transition region with the first slice thickness and a second slice thickness comprises the step of rotating the collimator to align the second collimator aperture with the x-ray source.

6. A method in accordance with claim 5 wherein scanning at least a portion the transition region with the first slice thickness and a second slice thickness comprises the steps of:

rotating the collimator so that the first collimator aperture directs the x-ray beam to at least a portion the transition region; and rotating the collimator to the second collimator aperture for a second slice thickness so that the second collimator aperture directs the x-ray beam to overlap a portion of the x-ray beam projected from the first collimator aperture.

7. A method in accordance with claim 1 wherein the imaging system includes an x-ray source for emitting an x-ray beam and a collimator for collimating the x-ray beam, the collimator including at least two opposing elements, and wherein scanning the object of interest with a first slice thickness comprises the step of spacing the collimator elements at a first distance apart.

8. A method in accordance with claim 7 wherein scanning at least a portion the transition region with the first slice thickness and a second slice thickness comprises the step of spacing the collimator elements at a second distance apart.

9. A method in accordance with claim 1 wherein the imaging system is configured to scan the object of interest with at least one helical pitch, and wherein collecting redundant data for the transition portion without interrupting the scan comprises the step of modifying the helical pitch.

10. A method in accordance with claim 1 wherein identifying a transition region comprises the step of measuring helical artifact inconsistencies.

11. A system for modifying slice thickness of a tomography system during a helical scan of an object of interest with an x-ray beam, the object of interest comprising a first region and a second region having a different structure than the first region, said system comprising a computer coupled to a gantry and to a patient table, the gantry having an opening and including an x-ray source generating an x-ray beam, a collimator, and a detector, the collimator comprising a first collimator aperture and at least a second collimator aperture, the collimator being rotatable relative to an x-ray source focal spot so that an x-ray beam collimated by the second collimator aperture overlaps a portion of the x-ray beam collimated by the first collimator aperture, said system configured to:

scan the first region of the object of interest with a first slice thickness;

identify a transition region intermediate the first region and the second region of the object of interest;

collect redundant data for the transition portion with first and second slice thickness without interrupting the scan; and scan the second region of the object of interest with the second slice thickness without interrupting the scan.

12. A system in accordance with claim 11 wherein to scan the object of interest with a first slice thickness, said system configured to translate the table through the gantry opening at a first table speed.

13. A system in accordance with claim 12 wherein to collect redundant data for the transition portion without interrupting the scan, said system configured to scan at least a portion the transition region with the first slice thickness and a second slice thickness without stopping the table translation.

14. A system in accordance with claim 13 wherein the first aperture defining a first slice thickness and the second aperture having a different size than the first aperture and defining a second slice thickness, and wherein to scan the object of interest with a first slice thickness, said system configured to align the collimator first aperture with the x-ray source.

15. A system in accordance with claim 14 wherein to scan at least a portion the transition region with the first slice thickness and a second slice thickness without stopping the table translation, said system configured to rotate the collimator to align the second collimator aperture with the x-ray source.

16. A system in accordance with claim 14 wherein to scan at least a portion the transition region with the first slice thickness and a second slice thickness, said system configured to:

rotate the collimator so that the first collimator aperture directs the x-ray beam to at least a portion the transition region; and rotate the collimator to the second collimator aperture for a second slice thickness so that the second collimator aperture directs the x-ray beam to overlap a portion of the x-ray beam projected from the first collimator aperture.

17. A system in accordance with claim 16 further comprising the step of sweeping the collimator so that the second collimator aperture directs the x-ray beam to overlap a portion of the x-ray beam projected from the first collimator aperture.

18. A system in accordance with claim 11 wherein the imaging system is configured to scan the object of interest with at least two helical pitches, and wherein to collect redundant data for the transition region without interrupting the scan, said system configured to scan the transition region portion with two helical pitches.

19. A system in accordance with claim 11 wherein to identify a transition region intermediate the first region and the second region of the object of interest, said system configured to dynamically determine a transition region during a scan.

20. A system in accordance with claim 11 wherein to identify a transition region, said system configured to perform a scout scan.

* * * * *